United States Patent [19]

Gero

[11] Patent Number: 4,692,143
[45] Date of Patent: Sep. 8, 1987

[54] UNIT PACKAGE CONTAINING READY-TO-USE VAGINAL CONTRACEPTIVE

[76] Inventor: Ilona B. Gero, 180 East End Ave., New York, N.Y. 10028

[21] Appl. No.: 864,497

[22] Filed: May 19, 1986

Related U.S. Application Data

[63] Continuation-in-part of Ser. No. 598,208, Apr. 9, 1984, abandoned.

[51] Int. Cl.$^4$ .......................................... A61M 31/00
[52] U.S. Cl. ...................................... 604/55; 604/286
[58] Field of Search ................ 604/55, 286, 287, 288, 604/359, 360, 368, 904

[56] References Cited

U.S. PATENT DOCUMENTS

| | | | |
|---|---|---|---|
| 3,490,545 | 1/1970 | Goldfarb et al. | 604/359 |
| 3,639,566 | 2/1972 | Naito et al. | 604/55 |
| 3,949,752 | 4/1976 | Van Stee | 604/286 |
| 4,228,797 | 10/1980 | Dickey | 604/55 |
| 4,351,338 | 9/1982 | Langlois et al. | 604/904 |
| 4,393,871 | 7/1983 | Vorhauer et al. | 604/55 |

Primary Examiner—C. Fred Rosenbaum
Assistant Examiner—Sherri Vinyard
Attorney, Agent, or Firm—Jacobs & Jacobs

[57] ABSTRACT

A premoistened ready-for-use vaginal contraceptive device and method of use thereof are described wherein a porous polyurethane sponge is provided which is impregnated with a bacteria-free sterile spermicide, pectin and pH control and swelling agent aqueous solution enclosed within and readily removable from a sealed packet and wherein the premoistened polyurethane sponge with its absorbed components when removed from the packet is immediately inserted in position and is ready for contraceptive use. After one or more coital episodes the sponge is removed, its effective life being up to about 24 hours. The spermicide is present in a maximum of 8% and the pectin constitutes about 5%, both percentages being based on the weight of the solution.

10 Claims, 6 Drawing Figures

UNIT PACKAGE CONTAINING READY-TO-USE VAGINAL CONTRACEPTIVE

RELATED APPLICATIONS

This application is a continuation in part of my copending application Ser. No. 598,208 filed Apr. 9, 1984 now abandoned the subject matter of which is incorporated herein by reference.

BACKGROUND OF THE INVENTION

Oral contraceptives of various types, particularly in "pill" form are well known and widely used because they have been found to be generally effective in the prevention of conception and it is further known that they can and do present risks of hormonal imbalances coupled with neurological disorders and other disadvantageous side effects. Spermicidal foams, gels and suppositories as well as diaphragms and IUD's are well known for preventing contraception.

Studies to find better and safer intravaginal contraceptives are constantly under investigation including a recently available device comprising a polyurethane disc having a central recess and containing 1,000 milligrams of a spermicide known as nonoxynol-9, chemically definable as nonylphenoxypoly (ethyleneoxy) ethanol. While generally comparable in effectiveness to a conventional diaphragm, the polyurethane disc device has serious drawbacks as set forth in my aforesaid copending application as it is capable of causing irritation and allergic reactions of sensitive tissue and the relatively large content of nonoxynol-9 has been found to be undesirable and even unsafe because it must be combined with water before use which may render the device non-sterile and the polyurethane disc is not reliably shape-stable in the presence of moisture and/or pressure due to its shape and relatively poor absorbent power or retention of substances coming into contact therewith.

NATURE OF THE PRESENT INVENTION

This invention relates to a sealed foil or plastic package containing a ready-to-use vaginal contraceptive comprising a sponge or spongy vaginal insert premoistened with a spermicidal composition and which insert, upon removal from its package, is positionable in and removable from the vagina at will and constitutes a safe, effective and reliable sterile non-toxic means for avoiding conception without harmful side effects.

In addition, the sponge-type intravaginal contraceptive of the present invention is designed to eliminate or substantially reduce the disadvantages of the polyurethane disc device as my novel contraceptive is individually packaged as a sterile, premoistened unit in a sealed, bacteria-free, foil packet with its spermicide already activated and instantly ready-for-use as the sponge is impregnated with a solution of sterile or distilled bacteria-free water so that the sponge is at all times sterile and uncontaminated and usable immediately upon removal from its packet. Thus, the sponge and its spermicide of the present invention is maintained sterile as it is out of contact with contaminants until ready for use; its dosage of spermicidal material is reliable, uniform and highly effective with a minimal amount of spermicide not greater than approximately 100 milligrams of nonoxynol-9, whereby optimal spermicidal action is quickly achieved and retained upon insertion of the premoistened sponge while minimizing or eliminating the possibility of irritation and other adverse or undesirable side effects on the vaginal vault while blocking access of semen or seminal fluids which could result in conception.

DESCRIPTION OF THE INVENTION

The present invention relates to a vaginal ready-for-use intravaginal contraceptive comprising, as a unit in an openable foil packet, a compressed or uncompressed porous, spongy mass suitable for manual or applicator insertion into the vaginal vault while ensuring maintenance of sterility. The spongy mass expands upon removal from its packet and is of appropriate size and shape and may, if desired, contain a swelling agent to achieve sufficient expansion to exert radial pressure against the vaginal wall and to block the cervix upon intravaginal insertion. The radial pressure maintains the contact established between the spongy mass and the vaginal wall and blocks access to the cervix, preventing dislodgment or mispositioning and providing an effective barrier against sperm penetration beyond the sponge without harmful effect on the female reproductive organs or adjacent tissue.

The spongy mass is preferably comprised of a polyurethane spheroidal sponge approximately 1.5 to 2.0 inches in diameter.

A drawstring or the like is attached to and extends from the sponge and provides means for withdrawal after use. The drawstring may be looped diametrically through and/or around the sponge and, when tightened, compresses an area or portion of the sponge.

The contraceptive sponge is immediately ready to be used upon removal from its sealed packet or container. This results, for example, from utilizing a sealed foil packet in which the contraceptive unit has the nonoxynol-9 spermicide which is already in solution absorbed in and held by the voids or pores of the sponge.

Sterility and freedom from bacteria prior to use are essential and are ensured by means of the use of a sealed packet container for the sponge and the bacteria-free, distilled water base in which the water-soluble spermicide is dissolved and enclosed in the container. The spermicidal action is achieved with no or a very minimum possibility of irritation to the vaginal vault or adjacent tissue by employing not more than about 100 milligrams of the nonylphenoxypoly (ethyleneoxy) ethanol in the sponge.

The spermicidal composition in the sealed packet with the sponge comprises, by weight, about 5% to 8% of nonylphenoxypoly (ethyleneoxy) ethanol and about 0.5 to 5% of pectin in a bacteria-free aqueous solution. Preferably, the composition comprises 8% of the nonylphenoxypoly (ethyleneoxy) ethanol and 0.5% of pectin in bacteria-free distilled water.

One of the major advantages of the invention is the inclusion of pectin in the spermicidal composition. Pectin (N.F.) is described in the National Formulary and is essentially a partially methoxylated polygalacturonic acid which conjugates with and detoxifies many toxins. It enzymatically degrades to acidic end products and thus enzymatically degrades in the vaginal vault to produce or maintain an acidic environment conducive to deodorization and the prevention or suppression of malodors from whatever source whether natural or unnatural or due to the presence of microorganisms or lactobacillary flora. The composition also contains at least one preservative and a pH adjusting agent and may, when necessary or desirable for sizing purposes of the sponge at its insertion, contain a cellulosic swelling agent such as sodium carboxymethylcellulose.

BRIEF DESCRIPTION OF THE DRAWINGS

In the accompanying drawings in which is shown a preferred embodiment of the invention.

DETAILED DESCRIPTION OF THE INVENTION AND ITS USE

Figure 1:
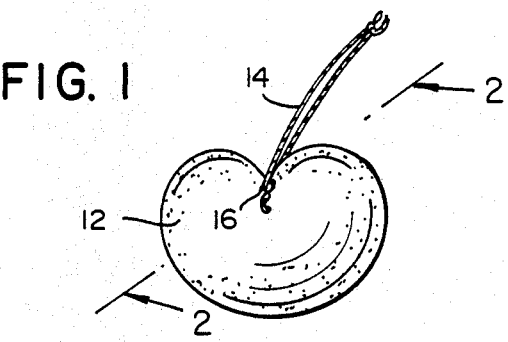
FIG. 1 is a perspective view of a vaginal contraceptive sponge and drawstring in accordance with the present invention.
Figure 2:
FIG. 2 is a sectional view taken substantially along the plane 2—2 of FIG. 1 and showing the drawstring looped diametrically through the sponge and compressing an upper area of the sponge.
Figure 3:
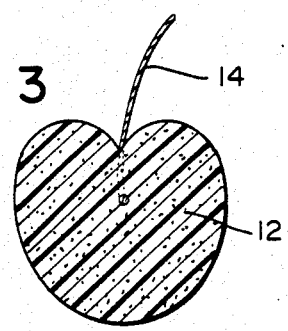
FIG. 3 is a sectional view taken substantially along line 3—3 of FIG. 2.

This invention is characterized by a unit foil or plastic packet sealing therein a spermicidally impregnated sponge which can be quickly or readily removed for immediate use. Approximately 100 milligrams of the spermicide, which is nonylphenoxypoly (ethyleneoxy) ethanol, is absorbed as a bacteria-free aqueous solution containing pectin and a preservative and pH control or swelling agent by the sponge and this reduced but effective amount of spermicide avoids irritation to the vaginal vault and ensures contraceptive protection.

The sponge, which is preferably a mass of porous polyurethane, is of appropriate size for intravaginal insertion and contains in the above solution absorbed therein a swelling or softening agent which causes expansion of the sponge sufficient to exert mild radial pressure against the vaginal wall and to block tbe cervix without adverse side effects. This prevents slippage or undesired movement or displacement from the intended position and maintains adequate contact between the sponge and the cervix of the female during and throughout its use. The sponge is free from discomfort to both sex partners and provides reliable spermicidal activity for 24 hours and through multiple coital episodes, following which it is removed and discarded.

A significant and highly important feature of the invention is the inclusion of pectin in the aqueous formulation absorbed by the sponge since it is biodegradable and a detoxicant as well as a deodorant and preventative of malodorous properties of vaginal flora. The naturally acidic environment which exists is maintained but may be supplemented by the addition of a pH adjusting agent.

The invention is extremely simple to use, is ready for immediate use upon removal from its packet and generally avoids any serious systemic side effects or physical discomfort.

Referring now to the drawings, reference numeral 10 denotes generally a vaginal contraceptive sponge enclosed in a sealed packet of foil or other suitable impervious material such as an aluminum-plastic laminate.

The sponge 12 is a generally spheroidal open-celled polyurethane mass having approximately 80 to 100 cells per lineal inch. A string 14 is looped diagonally through the sponge 12 and tied taut in a loop 16 for anchoring purposes. The tied loop 16 compresses and gathers a zone of the sponge and distorts its original spheroidal configuration as seen in the drawings. The looped string 14 forms a convenient means for withdrawing the sponge 12 from the vaginal vault after the sponge has served its intended purpose. A knot may be formed at the ends of the looped string 14 to form a second large loop and to assist the user in locating the looped string for withdrawing the sponge 12.

Figure 4:
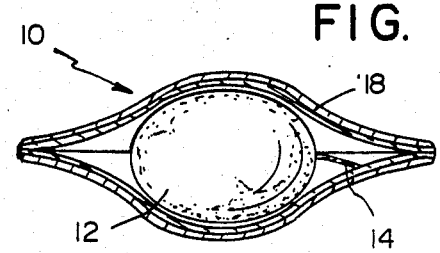
FIG. 4 is a vertical sectional view through a sealed rectangular packet showing the sponge enclosed therein and the upper and lower packet elements sealed at their meeting edges.

As best seen from FIG. 4, the sponge 12 is packaged in a hermetically sealed sterile foil packet 18 comprising two opposing sheets or films heat and/or pressure sealed around their periphery to form an enclosure for the sponge and to ensure sterility of the packet contents. The sponge 12 impregnated with a spermicide solution as referred to above is then encased in the packet 18 in a class 100 clean room for complete sterility. The packet 18 sheets may comprise a foil-thermoplastic film laminate sealed together around their periphery.

The spermicide absorbed by or impregnated into the sponge comprises a formulation, by weight, of about 5% to 8% nonylphenoxypoly (ethyleneoxy) ethanol, and about 0.5% to 5% of pectin, both in a sterile bacteria-free aqueous solution. Preferably, the solution comprises 8% of the nonylphenoxypoly (ethyleneoxy) ethanol and 0.5% of pectin in sterile bacteria-free distilled water together with the other additives or adjuvants. The pectin in addition to its advantages described above serves to control malodors, particularly odors accompanying trichomonas vaginalis and non-specific vaginitis. It is especially efficacious as a deodorizer for vaginal fluids and male semen and inhibits growth of vaginal flora and their odors due to vaginal pH changes. A pH adjusting agent such as glycine may also be employed as a constituent of the absorbed solution held in the voids or pores of the sponge and the glycine may cause a certain amount of gelatin of the pectin to avoid excessive fluidity.

The following table represents the preferred and best mode solution.

| Ingredient | SPERMICIDAL SOLUTION | |
|---|---|---|
| | Percentage by weight | Mg. Per Sponge |
| Nonylphenoxypoly (ethyleneoxy) ethanol | 8.000 | 100.0000 |
| Pectin | 0.500 | 6.2500 |
| Glycine | 0.500 | 6.2500 |
| Sodium Carboxymethylcellulose | 0.125 | 1.5625 |
| Methylparaben (q.s.) | 0.050 | .6250 |
| Lactic Acid (q.s.) | 0.050 | .6250 |
| Sodium Benzoate (q.s.) | 0,100 | 1.2500 |
| Distilled Water | 90.675 | 1,133.4375 |
| TOTAL | 100.000% | 1,250.0000 mg. |

The methylparaben acts as a preservative useful against molds, fungi and yeast. It is also useful against gram positive bacteria.

The sodium benzoate is a preservative which is also useful as a urinary antiseptic against bacteria and molds.

The lactic acid is a bactericide useful in the prevention of leucorrhoea and tends to maintain a pH normal for vaginal fluids.

The pectin is further useful as an emulsifier and stabilizer and aids in the formation and maintenance of a uniform solution of suitable consistency.

The sponge 12 is ready for immediate use upon its removal from the packet 18 since it contains and carries in its pores and voids the active spermicidal solution. The sponge has a minimum uncompressed peripheral dimension in a transverse diametrical plane of 1.5 to 2.0 inches.

Figure 5:
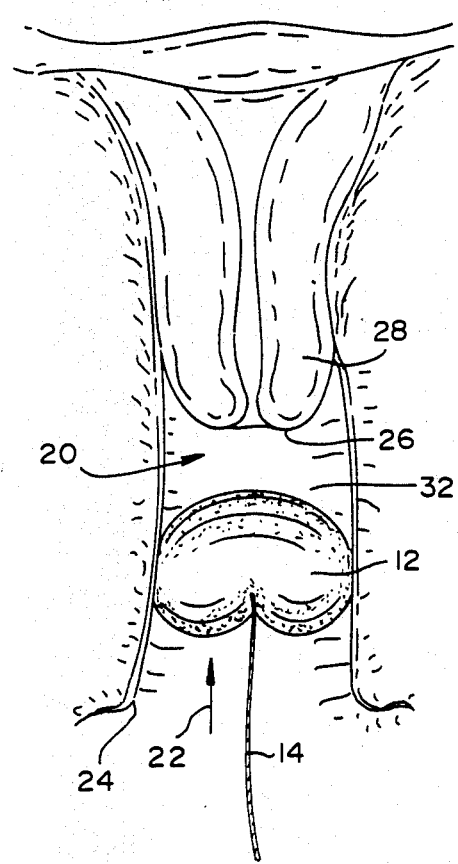
FIG. 5 is a schematic view taken through the vaginal vault and showing the sponge being inserted.
Figure 6:
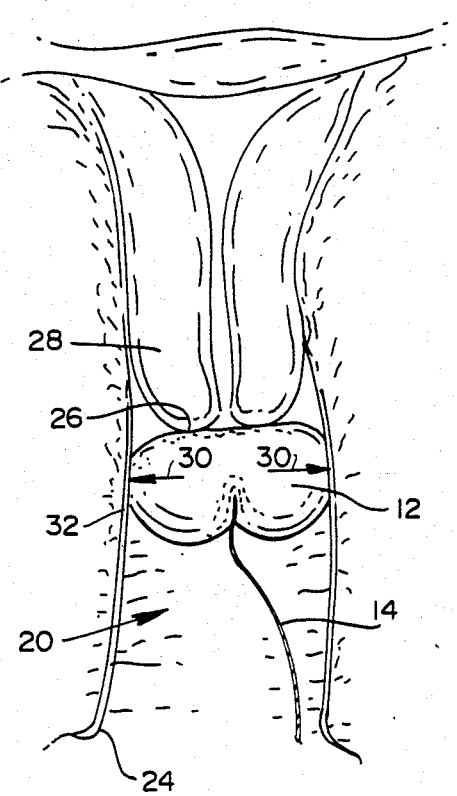
FIG. 6 is a view similar to FIG. 5 showing the sponge in operative position in contact with the cervix and sealing the vaginal wall.

In use the premoistened, ready-for-use sponge 12 as removed from its packet, is gently compressed and is then immediately urged upwardly into the vaginal vault 20, as indicated by the arrow 22, beyond the vaginal mouth 24 until it abuts the lips 26 of the cervix 28. Such positioning is depicted in FIG. 5, and the final position is shown in FIG. 6, in which the arrows 30 illustrate an important function of the contraceptive in that the sponge 12 is sufficiently wide to fill the void across the vaginal wall 32 and exerts mild pressure thereagainst. A minimum uncompressed transverse dimension of approximately 1.8 inches is compatible with practically all women. The transverse dimension of the sponge, wherein the sponge dimension is measured, may typically comprise the horizontal plane shown by arrows 30 or any other plane which passes through the sponge when in peripheral contact with the vaginal wall 32.

It is understood that the impregnated sponge 12 may contain a swelling agent as a component of the solution. Sodium carboxymethylcellulose or other suitable water-soluble cellulose derivative such as methyl cellulose are exemplary to assist in creating adequate but gentle radial sponge expansion and pressure (schematically illustrated by the arrows 30) against the vaginal wall 32. Such pressure assures that the sponge 12 will fit snugly within the vaginal vault 20 without causing tissue irritation or slippage during and after intercourse. The snug fit provides that the sponge 12 will be maintained in its abutting contact with the lips of the cervix 28. In this position, the sponge 12 will prevent passage of sperm around the vaginal wall 32 and will block entrance of sperm into the womb.

The sponge 12 may be retained in place and provide contraceptive spermicidal activity for 24 hours. It may be removed from the vaginal vault 20 by grasping the looped string 14 and pulling downwardly. The knot, which may be located adjacent the end of the drawstring, is useful in locating and pulling the drawstring.

The method of utilizing the sponge contraceptive will be clear from the foregoing description.

With respect to the constituents of the spermicidal formulation, the nonylphenoxypoly (ethyleneoxy) ethanol may be obtained from Rohm & Haas Company under the trademark Triton N-101. All of the constituent ingredients of the spermicidal formulation are USP grade and are obtainable from conventional sources. With respect to the sponge 12, suitable polyurethane sponge spheres are obtainable from the Scott Foam Division of the Scott Paper Co.

Thus, it will be seen that there is provided a premoistened, ready-for-use sterile and harmless intravaginal sponge contraceptive capable of effective prevention of conception for up to about 24 hours after which it is removed and discarded.

It is understood that the foregoing is typical or exemplary and not limitative and that various modificatifons may be made without departing from the invention as defined by the subjoined claims.

What is claimed is:

1. A vaginal contraceptive device comprising a sealed packet enclosing therein a porous polyurethane sponge premoistened prior to enclosure in the packet with a sterile bacteria-free aqueous solution of a small but spermicidally effective amount of a water-soluble spermicide, pectin and a pH control and swelling agent and preservative, the sealed packet being readily rupturable for removal of the porous polyurethane sponge with its absorbed components which is immediately ready for use by intravaginal insertion for the prevention of conception during coitus over a period of time up to about 24 hours, said premoistened polyurethane sponge after removal from said packet assuming dimensions exerting non-irritating pressure against the vaginal wall of the user and blocking entrance to the cervix when inserted, means being provided for removing the sponge at will after use.

2. A vaginal contraceptive device according to claim 1 wherein the spermicide is nonylphenoxypoly (ethyleneoxy) ethanol.

3. A vaginal contraceptive device according to claim 2 wherein the nonylphenoxypoly (ethyleneoxy) ethanol is in an amount by weight of the premoistening solution in the range of about 5% to a maximum of about 8%.

4. A vaginal contraceptive device according to claim 3 wherein the spermicide is nonylphenoxypoly (ethyleneoxy) ethanol and the pectin is present in the solution in the amount of about 0.5 to 5%.

5. A vaginal contraceptive device according to claim 1 wherein the spermicide is nonylphenoxypoly (ethyleneoxy) ethanol in an amount by weight of the premoistening solution of about 8% and the pectin is present in the solution in the amount of about 0.5%.

6. In a vaginal contraceptive device having contraceptive means in a sealed packet, said contraceptive means comprising a porous polyurethane sponge premoistened prior to enclosure in the packet with a sterile bacteria-free aqueous solution of a small but spermicidally effective amount of a water-soluble spermicide, pectin and a pH control and swelling agent and preservative, the sealed packet being readily rupturable for removal of the porous polyurethane sponge with its absorbed components which is immediately ready for use by intravaginal insertion for the prevention of conception during coitus over a period of time up to about 24 hours, said premoistened polyurethane sponge being of such dimensions as to exert non-irritating pressure against the vaginal wall of the user and to block entrance to the cervix when inserted, and provided with means for removing it at will after use.

7. An intravaginal contraceptive method which comprises intravaginally inserting a porous polyurethane sponge premoistened prior to enclosure in a packet with a sterile bacteria-free aqueous solution of a small but spermicidally effective amount of a water-soluble spermicide, pectin and a pH control and swelling agent and preservative, rupturing the sealed packet and removing the porous polyurethane sponge with its absorbed components which is then immediately ready for use by intravaginal insertion for the prevention of conception during coitus over a period of time up to about 24 hours, inserting the de-packeted premoistened sponge into position for contraception, said premoistened polyurethane sponge being of such dimensions as to exert non-irritating pressure against the vaginal wall of the user and to block entrance to the cervix when inserted, and removing the used sponge at will after use.

8. A premoistened porous polyurethane sponge dimensioned to exert mild pressure against the vaginal wall and to block access to the cervix of the user, said sponge being impregnated with a sterile, bacteria-free aqueous solution containing, by weight of the solution, about 5 to 8% of a spermicide, about 0.5 to 5% of pectin and a preservative and pH control and swelling agent, said impregnated sponge being sealed in a foil packet which is readily rupturable to provide an immediately ready-to-use contraceptive sponge insertable intravaginally to prevent conception over a period of time up to 24 hours and removable at will, and said impregnated contraceptive sponge being free of irritating, toxic or adverse hormonal side effects.

9. A premoistened porous polyurethane sponge according to claim 8, wherein the spermicide is nonylphenoxypoly (ethyleneoxy) ethanol in the amount of about 8% and the pectin amounts to about 0.5%.

10. A premoistened porous polyurethane sponge according to claim 9, wherein the impregnating solution is a spermicidal solution having the following ingredients in the following proportions, by weight of the solution:

| Ingredient | Percentage by weight | Mg. per Sponge |
|---|---|---|
| Nonylphenoxypoly (ethyleneoxy) ethanol | 8.000 | 100.0000 |
| Pectin | 0.500 | 6.2500 |
| Glycine | 0.500 | 6.2500 |
| Sodium Carboxymethylcellulose | 0.125 | 1.5625 |
| Methylparaben (q.s.) | 0.050 | .6250 |
| Lactic Acid (q.s.) | 0.050 | .6250 |
| Sodium Benzoate (q.s.) | 0.100 | 1.2500 |
| Distilled Water | 90.675 | 1,133.4375 |
| TOTAL | 100.000% | 1,250.0000 mg. |

* * * * *